United States Patent [19]

Bechara et al.

[11] 4,430,456

[45] Feb. 7, 1984

[54] POLYURETHANE-FORMING PROCESS USING AMINO AND AMIDO DIALKYL TIN CARBOXYLATES

[75] Inventors: Ibrahim S. Bechara, Boothwyn; Rocco L. Mascioli, Media, both of Pa.

[73] Assignee: Air Products and Chemicals, Inc., Allentown, Pa.

[21] Appl. No.: 418,519

[22] Filed: Sep. 16, 1982

Related U.S. Application Data

[62] Division of Ser. No. 230,849, Feb. 2, 1981, Pat. No. 4,360,670.

[51] Int. Cl.$^3$ .................. C08G 18/14; C08G 18/24; C07F 7/22; C07D 207/00
[52] U.S. Cl. .................. 521/128; 252/182; 521/129; 528/53; 528/54; 544/64; 548/403; 548/573
[58] Field of Search .................. 528/53, 54; 521/128, 521/129; 252/182

[56] References Cited

U.S. PATENT DOCUMENTS

| | | |
|---|---|---|
| 2,704,756 | 3/1955 | Leistner et al. .................. 544/64 |
| 2,820,053 | 1/1958 | Hotten .................. 260/429 R |
| 2,977,379 | 3/1961 | Dorfelt et al. .................. 523/122 |
| 3,067,167 | 12/1962 | Lynn et al. .................. 524/178 |
| 3,164,557 | 1/1965 | Merten et al. .................. 521/126 |
| 3,355,469 | 11/1967 | Herbstmann .................. 521/126 |
| 3,365,477 | 1/1968 | Gee et al. .................. 260/429 R |
| 3,538,088 | 11/1970 | Hartmann .................. 544/64 |
| 3,681,271 | 8/1972 | Yokoo et al. .................. 521/126 |
| 3,703,484 | 11/1972 | Keshi et al. .................. 521/126 |
| 3,796,674 | 3/1974 | Lengnick et al. .................. 521/126 |
| 4,077,941 | 3/1978 | Stephen et al. .................. 524/204 |

FOREIGN PATENT DOCUMENTS 899949 6/1962 United Kingdom .

*Primary Examiner*—H. S. Cockeram
*Attorney, Agent, or Firm*—Michael Leach; E. Eugene Innis; James C. Simmons

[57] ABSTRACT

Amino and amido dialkyltin dicarboxylates and stannoxy carboxylates are prepared by first reacting an amine or amino alcohol with a dicarboxylic acid anhydride, followed by reaction of the resulting product with a dialkyltin oxide. The obtained compounds are useful as catalysts for promoting reaction of organic isocyanates with organic compounds having one or more active hydrogen-containing groups.

12 Claims, No Drawings

POLYURETHANE-FORMING PROCESS USING AMINO AND AMIDO DIALKYL TIN CARBOXYLATES

This is a division of application Ser. No. 230,849, filed Feb. 2, 1981, now U.S. Pat. No. 4,360,670.

The present invention relates to catalyzing the reaction between organic isocyanates with organic compounds containing an active hydrogen group and is particularly concerned with the preparation of stable organo tin catalysts of high activity for use in production of polyurethanes.

BACKGROUND OF PRIOR ART

A wide variety of tin carboxylate compounds have been proposed for use as catalysts in the preparation of polyurethanes. Certain of these are in commercial use, either alone or as co-catalysts with tertiary amine catalysts. U.S. Pat. No. 3,164,557, proposes certain organotin compounds containing a tertiary nitrogen atom for use as polyurethane catalysts. The compounds in said patent correspond to the general formula

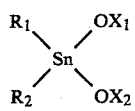

wherein $R_1$ and $R_2$ are hydrocarbon radicals and $X_1$ and $X_2$ are stated to be organic radicals, at least one of which contains a tertiary nitrogen atom. Typical of the tin compounds thus proposed is

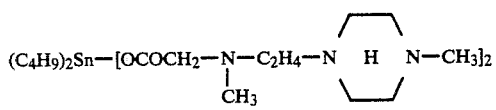

The use of organotin compounds containing tertiary nitrogen is also disclosed in British Pat. No. 899,948. The compounds therein disclosed are either unstable amino alkoxides containing a

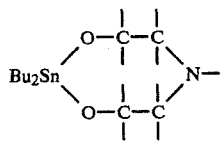

group (prepared from an alkanolamine and a tin oxide) or amino carbonates having a tin nitrogen bond. The tin nitrogen bond is much less stable than that in tin carboxylates.

Organo-substituted tin amino-carbamates, which are proposed for use as catalysts in preparation of polyurethane foams according to U.S. Pat. No. 3,796,674, also contain a tin nitrogen bond. The polyurethane foam catalysts disclosed in U.S. Pat. Nos. 3,681,271 and 3,703,484 are stannoxane type compounds, prepared by reacting a diallkyltin oxide with an acid or acid derivative. According to the earlier of these patents, the presence of a

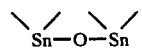

bond boosts the catalytic activity.

BRIEF SUMMARY OF THE INVENTION

It has now been found, in accordance with the present invention, that organotin compounds of unexpectedly high catalytic activity and good stability are had, when such compounds contain one or more functional groups from among

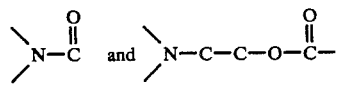

as obtained, for example, by reaction of a tin oxide with an amido acid or an amino acid ester of the types:

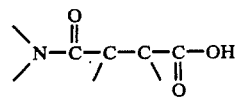

or

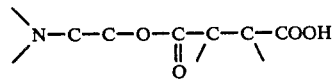

The compounds produced in accordance with the invention correspond respectively to either of the generic formulas

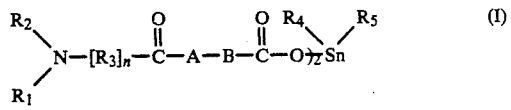  (I)

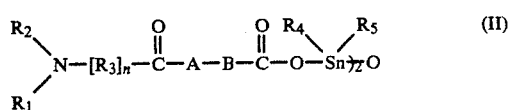  (II)

wherein $R_1$ and $R_2$ are independently H, alkyl groups of 1 to 20 carbon atoms; hydroxyalkyl or alkoxyalkyl of 2 to 20 carbon atoms; or $R_1$ and $R_2$, together form a heterocyclic ring of 5 or 6 atoms;

$R_3$ is a $-CH_2-CH(R_6)-O-$ group in which n=zero or one and $R_6$ is hydrogen or an alkyl or an alkyl hydrocarbyl group of up to 20 carbon atoms;

A and B are carbon atoms linked by a single or double bound or together comprise part of a six membered ring from the group consisting of cyclohexane, cyclohexene and benzene;

$R_4$ and $R_5$ are independently alkyl groups of 1 to 20 carbon atoms, phenyl, or cyclo alkyl groups of 6 to 20 carbon atoms.

The invention includes these novel compounds as such and methods for their preparation, as well as methods and compositions for the use of these organotin compounds as catalysts, alone or in combination with other catalysts, for isocyanate reaction with active hydrogen containing compounds, such as in the preparation of polyurethanes.

DETAILED DESCRIPTION OF THE INVENTION

The compounds of the present invention can be prepared in two steps. In the first step, an amine or an amino alcohol is reacted with an acid anhydride, respectively in accordance with the following equations:

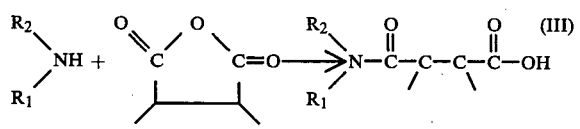

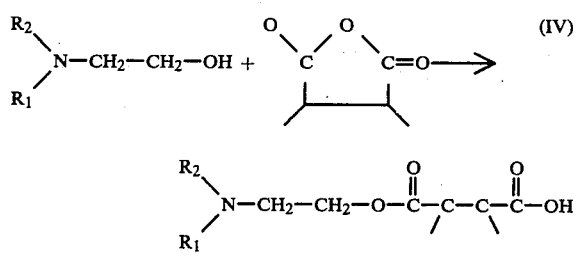

In the next step the compound produced in equation III or that in equation IV above, respectively, is reacted with a dialkyltin oxide, thus:

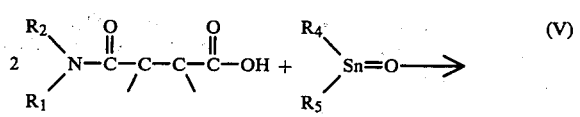

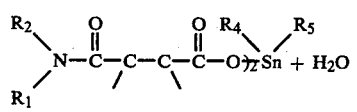

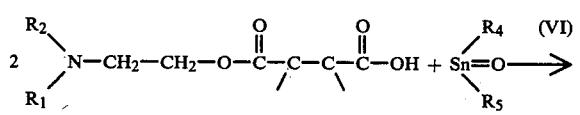

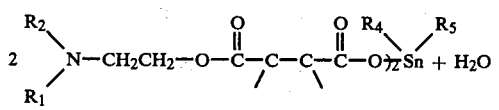

By reacting only one mole of the amido or amino compound per mole of dialkyltin oxide, the compounds obtained correspond respectively to that shown in equations VII and VIII below:

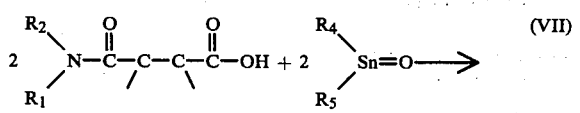

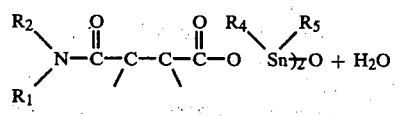

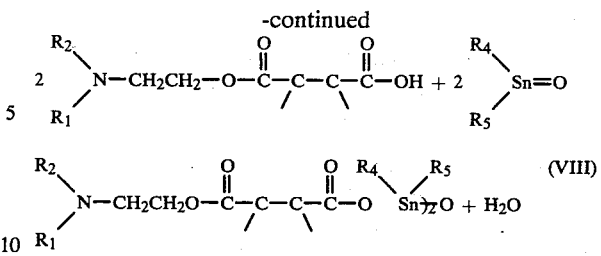

The following examples illustrate preparation of the novel compounds of the invention.

EXAMPLE 1

Into a 1 liter 3-neck, round bottom flask was charged 100 gs (1 mole) of succinic anhydride and 400–500 cc of toluene. The flask was then equipped with a mechanical stirrer and a reflux condenser mounted on a Dean-Stark trap and an addition funnel. The flask was heated with stirring to 120° C. When the succinic anhydride was completely dissolved, 89 gs (1 mole) of dimethylethanolamine (DMEA) were added slowly. After the addition of the amine was completed, the reaction mixture was cooled to 70° C. and 125 gs (½ mole) of dibutyltin oxide were added and the reaction mixture reheated to the refluxing point of toluene and the azeotroped water collected in the Dean-Stark trap. A total of 12 gs of water was collected after 4 hours. The reaction was cooled again to room temperature and the toluene removed on a rotovac. The viscous pale residue weighed 301.4 gs. It was analyzed by infrared and nuclear magnetic resonance spectroscopy. The composition of this product was:

60.9 mole % of

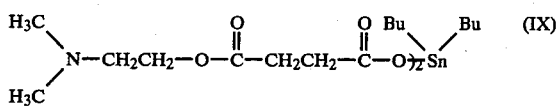

11.3 mole % succinic acid
27.8 mole % toluene

EXAMPLES 2 and 3

The same apparatus was used as in Example 1. The materials charged were 1 mole of tetrahydrophthalic anhydride and 300 cc of toluene. The toluene was gently heated to reflux until all the anhydride was dissolved; then 1 mole of dialkylalkanol amine (either diethylethanol amine or DMEA) was added from an addition funnel slowly over a period of about 1 hour. The reaction mixture was then cooled to about 50° C. and ½ mole of dibutyltin oxide was added rapidly. The reaction mixture was then refluxed again and the water formed azeotroped out into the Dean-Stark trap. When the theoretical amount of water ½ mole (9 cc) was removed, the reaction mixture was transferred to a rotovac where the toluene was removed under reduced pressure. The residue was weighed and analyzed by infrared and nuclear magnetic resonance spectroscopy. The infrared spectra showed ester carbonyl bands at 1725 cm$^{-1}$. It also showed the total absence of —OH and anhydride carbonyl bands, indicating the complete reaction of alkanolamine with the anhydride and dibutyltin oxide and suggesting the following structure:

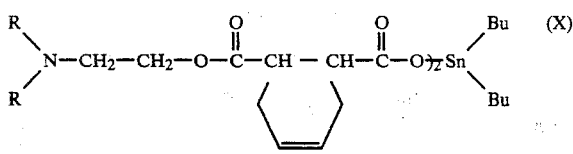

This structure was further confirmed by NMR and elemental analysis as shown in Table I below:

TABLE I

| Example | Amine Used | Elemental Analysis | Calculated | Found | Refractive Index at 25° C. |
|---|---|---|---|---|---|
| 2 | diethyl-ethanol-amine | C | 56.17 | 56.22 | 1.5150 |
| | | H | 8.08 | 8.16 | |
| | | N | 3.45 | 3.45 | |
| | | Sn | 15.4 | 14.65 ± .17 | |
| 3 | dimethyl-ethanol-amine | C | 53.71 | 52.61 | 1.5073 |
| | | H | 7.83 | 7.64 | |
| | | N | 3.92 | 3.15 | |
| | | Sn | 16.64 | 17.02 ± 0.03 | |

EXAMPLE 4

The apparatus and procedure used were the same as in Examples 2 and 3 except the amine was dibutyl amine and the resulting product had the amido structure.

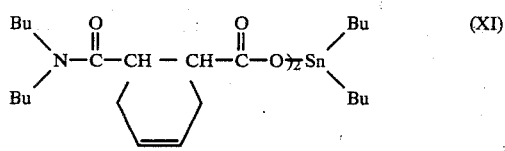

The infrared analysis shows the absence of OH and anhydride carbonyl, and the nuclear magnetic resonance spectra shows 86 mole % of structure XI and 14 mole % toluene in the crude product. The refractive index at 22° C. is 1.5076. Elemental analysis on a purified sample was as follows: Calculated for Molecule XI: C—60.53%, H—8.82%, N—3.53%, Sn—15.00%. Found: C—60.74%, H—8.95%, N—3.27%, Sn—15.15±0.05.

EXAMPLE 5

The same procedure and apparatus were employed in this example as those of Example 4, except the amine was N,N-bis-hydroxyethylamine (commonly known as diethanolamine). Diglyme (124 g per 105 g DEA) was also used as co-solvent with toluene. At the end of the reaction and after the theoretical amount of water was azeotroped out, the reaction mixture was cooled to room temperature. The product separated out as a gummy bottom layer. Yield=38.8% of theoretical. This product was analyzed for structure XII.

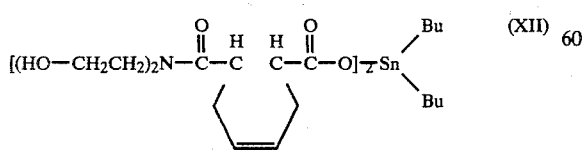

Calculated for structure XII: C—51.54, H—7.24, N—3.76, Sn—15.97. Found: C—56.22, H—8.16, N—3,45, Sn—15.3±0.12.

EXAMPLE 6

Using an apparatus similar to the one described in Example 1, 309.4 gs (2 moles) of cyclohexane dicarboxylic acid anhydride was reacted with 259.8 gs (2 moles) of dibutyl amine in 422.8 gs of toluene. The resulting amido carboxylic acid was then reacted in situ with 498.0 gs (2 moles) of dibutyltin oxide. Total reaction time was 4 hours. The amount of water removed was 18.5 cc (1 mole). The weight of the product recovered was 1026.0 g and % recovery 97.8. The IR of the product shows the absence of any NH or OH bands, and it shows the characteristic amid and carboxylate carbonyl absorptions. This coupled with the amount of water obtained suggests the stannoxy carboxylate structure XIII Refractive index at 25° C. was 1.5112.

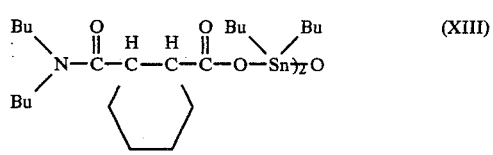

The nuclear magnetic resonance analysis also supports the above structure. It shows the methylene on nitrogen proton at 3.2 ppm with an area/H=0.77. It also shows the rest of the protons at 0.7-2.0 ppm with an area/H=0.77.

EXAMPLES 7-11

The same procedure was used as Examples 2-4 except that the molar ratio of the amine to anhydride to dibutyltin oxide was changed to 1:1:1. In this method ½ mole of water was obtained per 1 mole of dibutyltin oxide and the products obtained have the general structure:

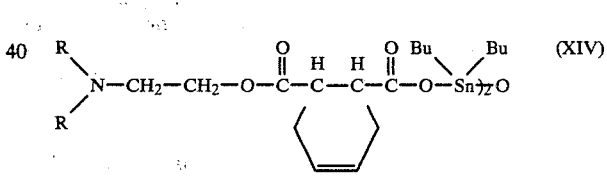

Table II below lists the various amines used in this preparation.

TABLE II

| Example | Amine | Anhydride | Refractive Index @ 25° C. | Elemental Analysis in Wt. % (Calc'd) | (Found) |
|---|---|---|---|---|---|
| 7 | DMEA | Tetrahydrophthalic | 1.5175 | C 49.90 | 50.02 |
| | | | | H 7.48 | 7.57 |
| | | | | N 2.91 | 2.33 |
| | | | | Sn 24.74 | 25.3 ± 0.04 |
| 8 | Diethylethanolamine | Tetrahydrophthalic | 1.4869 | | |
| 9 | Dimethylaminopropanol | Tetrahydrophthalic | 1.4865 | | |
| 10 | B—hydroxyethyl morpholine | Tetrahydrophthalic | 22° C. 1.5244 | | |
| 11 | Dimethyl isopropanolamine | Tetrahydrophthal- | 22° C. 1.5180 | C 50.91 | 50.65 |
| | | | | H 7.68 | 7.43 |
| | | | | N 2.83 | 1.52 |

TABLE II-continued

| Example | Amine | Anhydride | Refractive Index @ 25° C. | Elemental Analysis in Wt. % (Calc'd) | (Found) |
|---|---|---|---|---|---|
| | | ic | | Sn 24.04 | 24.74 |

The infrared spectra of these compounds also show the absence of OH and anhydride bands and show the ester carbonyl bands at ~1725-1730 cm$^{-1}$. Nuclear magnetic resonance analysis also confirms the above structure (XIV). An example of NMR analysis is shown in Table III.

TABLE III
NMR analysis for structure (Example 10)

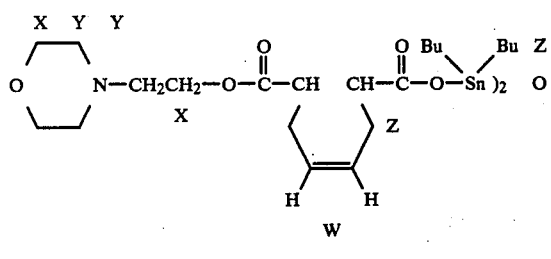

| Type of Protons | Chemical Shift | No. of Protons | Area/H |
|---|---|---|---|
| X | 4.5–3.5 | 6 | 3.5 |
| Y | 3.5–2.2 | 12 | 4.3 |
| Z | 2.2–0.6 | 18 | 4.3 |
| W | 5.7 | 2 | 2.5* |

Total Count 159 for 38 protons which is 4.2/proton.
*While this integration figure is less than it should be, the operator believes it is due to a problem in the instrument.

EXAMPLE 12

The procedure employed in this example was the same as in examples 7–11 except that the amine was dimethyl ethanol amine and the anhydride was cyclohexane-1,2-dicarboxylic acid anhydride. The product obtained has the structure of type (XV).

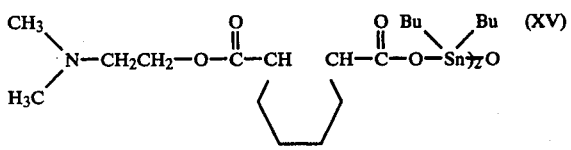

Infrared analysis shows the expected ester carbonyl bands at 1725-1730 cm$^-$ and the absence of the OH and anhydride carbonyl band. The nuclear magnetic resonance analysis shows the expected chemical shift for all the protons of the above molecules. The NMR analysis also shows toluene contaminants.

EXAMPLE 13

Following the same procedure as in Example 12, dimethylethanol amine, cyclohexane 1,2-dicarboxylic acidanhydride and dibutyltin oxide were reacted in 1:1:½ molar ratios respectively. One mole of water per mole of tin oxide was obtained. The product was analyzed by IR and NMR spectroscopy and confirmed to be of structure (XVI). Further confirmation was obtained from elemental analysis. The analysis in wt. % for Molecule XVI was: Calculated: C—53.56, H—8.09, N—3.91, Sn—16.59. Found: C—32.92, H—8.29, N—3.53, Sn—15.94±0.12.

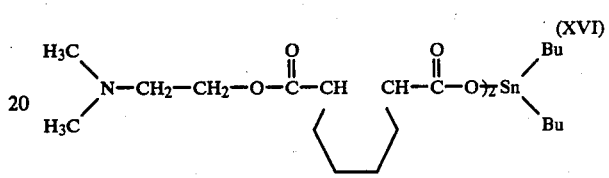

The compounds of the present invention were found to be useful as catalysts for isocyanate alcohol and isocyanate water reaction. In general, these compounds are effective catalysts for the reaction of isocyanate with active hydrogen containing compounds. They are superior in catalytic activity and hydrolytic stability to standard catalysts such as dibutyltin dilaurate used in the preparation of urethane polymers. The following examples demonstrate the effectiveness and other advantages of these compounds in catalyzing urethane polymer forming reactions.

EXAMPLE 14

In this example a flexible foam formulation was chosen to evaluate the catalysts of the present invention. The "one shot" hand mix technique was used in the preparation of foams. The composition of this formulation is shown below.

| Formulation 1 | |
|---|---|
| Components | pbw |
| (1) Voranol 3010 | 173.0 |
| Water | 7.8 |
| (2) Silicone L-6202 | 2.7 |
| (3) Hylene TM | 90.0 |
| Catalysts | as shown in Table IV |

TABLE IV

| | Catalysts Used and Their Activities in Formulation 1 | | | | | |
|---|---|---|---|---|---|---|
| Catalyst | pbw/184 gr Resin | | | | | |
| (4) DABCO 33-LV | 0.5 | | | | | |
| (5) T-9 | 0.3 | | | | | |
| Example 6 | | 0.75 | | | | |
| Example 13 | | | 0.75 | | | |
| Example 12 | | | | 0.38 | | |
| Example 10 | | | | | 0.75 | |
| Example 7 | | | | | | 0.38 |
| Reactivity | | | | | | |
| Cream time (secs.) | 13 | 16 | 16 | 16 | 16 | 16 |
| Hard Gel Time (secs.) | 85/87 | 100/105 | 80/85 | 85/90 | 80/85 | 84/86 |

TABLE IV-continued

| Catalyst | Catalysts Used and Their Activities in Formulation 1 pbw/184 gr Resin | | | | | |
|---|---|---|---|---|---|---|
| Rise time (secs.) | 75 | 90 | 78 | 80 | 72 | 76 |
| Physical Properties | | | | | | |
| Density lbs/cu ft | 1.3 | 1.29 | 1.27 | 1.27 | 1.29 | 1.25 |
| Air flow cu ft/min | 5.35 | 4.70 | 1.31 | 4.0 | 3.15 | 1.53 |
| Number of cells/inch | 54.5 | 53.0 | 55.0 | 55.0 | 62.0 | 56 |
| Tear lbs/inch | 2.76 | 2.15 | 2.74 | 2.07 | 2.25 | 2.31 |
| % Elongation | 207 | 99 | 215 | 151 | 125 | 174 |

(1) Voranal 3010 is a triol of 3000 M. Wt; hydroxy no. 54.4–58.4; marketed by Dow Chemical Company.
(2) Silicone L-6202 is a surfactant marketed by Union Carbide.
(3) Hylene TM is DuPont's trade name for toluene diisocyanate.
(4) DABCO 33-LV is trademark for triethylenediamine; marketed by Air Products.
(5) T-9 is stannous octoate; marketed by M&T It can be seen from the above example that good flexible foams can be made by the catalysts of the present invention at considerably lower concentration than the control. Also, it is important to note that flexible foams were made by these catalysts alone and without the addition of the usually expensive amine co-catalyst. In certain urethane formulations tertiary amine catalysts are best employed together with organotin compounds. The tin compounds of the invention may be similarly used in such co-catalyst systems, often with advantages over the previously employed tin compounds, as will hereinafter appear.

EXAMPLE 15

The compounds of the invention were evaluated in rigid foam formulation 2 by the "one shot" hand mix technique. The reactivity of the catalysts was compared to standard rigid urethane catalysts and is shown in Table V.

The data of Tables V and VI show that the compounds of the present invention are as good catalysts for preparing rigid urethane foams as standard commercial catalysts.

EXAMPLE 16

The compounds of the present invention were evaluated in yet another rigid foam formulation using the "one shot" method and by hand mix techniques. The formulation used was that of 3, and the reactivity and physical properties obtained on these foams are shown in Tables VII and VIII.

Again, the data demonstrate the effectiveness of these compounds in the preparation of rigid urethane foams.

TABLE V

| RIGID FOAM DATA | 1 | 2 | 3 | 4 | 5 | 6 | 7 | 8 |
|---|---|---|---|---|---|---|---|---|
| Temp., °C. | 31 | 31 | 31 | 31 | 31 | 32 | 32 | 32 |
| Polycat 8 | .8 | — | — | — | — | — | — | — |
| Rigid Foam Premix (g) | 157.5 | 157.5 | 157.5 | 157.5 | 157.5 | 157.5 | 157.5 | 157.5 |
| 50% (Ex 13) | — | .5 | .3 | .1 | .2 | — | — | — |
| 50% (Ex 12) | | | | | | .3 | .15 | .10 |
| 50% (Ex 10) | | | | | | | | |
| 75% (Ex 7) 25% Diglyme | | | | | | | | |
| 50% T-1 D.P.G. | | | | | | | | |
| 50% (Ex 6) 50% T-12 D.P.G. | | | | | | | | |
| Hylene TIC (g) | 105 | 105 | 105 | 105 | 105 | 105 | 105 | 105 |
| Initial | 13 | 13 | 13 | 15 | 14 | 13 | 14 | 15 |
| Strings | 47/50 | 35/40 | 35 | 50 | 40 | 30/35 | 40 | 50 |
| Tack Free | 65 | 40/45 | 45 | 80 | 60 | 40 | 55/60 | 75 |
| Rise | 115 | 90 | 90 | 120 | 115 | 85 | 90 | 110 |
| | 9 | 10 | 11 | 12 | 13 | 14 | 15 | 16 |
| Temp., °C. | 32 | 32 | 32 | 32 | 32 | 32 | 32 | 32 |
| Polycat 8 | — | — | — | — | — | — | — | .8 |
| Rigid Foam Premix (g) | 157.5 | 157.5 | 157.5 | 157.5 | 157.5 | 157.5 | 157.5 | 157.5 |
| 50% (Ex 13) | — | — | — | — | — | — | — | — |
| 50% (Ex 12) | — | — | — | — | — | — | — | — |
| 50% (Ex 10) | .15 | — | — | — | — | — | — | — |
| 75% (Ex 7) 25% Diglyme | | .15 | — | — | — | — | .10 | — |
| 50% T-1 D.P.G. | | | | .15 | .10 | — | — | — |
| 50% (Ex 6) 50% T-12 D.P.G. | | | | | | .15 | — | — |
| | | | | | | | .10 | — |
| Hylene TIC (g) | 105 | 105 | 105 | 105 | 105 | 105 | 105 | 105 |

TABLE V-continued

| RIGID FOAM DATA | | | | | | | | |
|---|---|---|---|---|---|---|---|---|
| Initial | 15 | 14 | 14 | 15 | 15 | 15 | 15 | 13 |
| Strings | 45 | 35 | 40 | 40 | 50 | 50 | 45 | 47/50 |
| Tack Free | 65 | 50 | 55 | 65 | 80/85 | 85 | 80 | 65 |
| Rise | 105 | 100 | 100 | 105 | 110 | 115 | 115 | 113/115 |

TABLE VI

Physical Properties on Hand Mixed Rigid Foams Made with Amino and Amidotin Carboxylates

| Formulation 2 | pbw |
|---|---|
| [6]Selectrofoam 6406 | 109 |
| [7]DC-193 | 1.5 |
| [8]Freon 11B | 47 |
| Catalyst | As Shown |
| [9]Hylene TIC | 105 |

| Catalyst | Concentration, pbw | | | | | | |
|---|---|---|---|---|---|---|---|
| [10]Polycat 8 | 0.8 | | | | | | |
| Example 13 | | 0.1 | | | | | |
| Example 12 | | | 0.1 | | | | |
| Example 10 | | | | 0.15 | | | |
| Example 6 | | | | | 0.15 | | |
| Example 7 | | | | | | 0.1 | |
| [11]T-12 | | | | | | | 0.1 |
| Density, lbs/cu.ft. | 1.41 | 1.44 | 1.40 | 1.42 | 1.44 | 1.41 | 1.42 |
| Cell Count/Inch | 65 | 65 | 50 | 65 | 75 | 85 | 90 |
| Dimensional Stability at 158° F. @ 100% R.H. After 7 Days | 13.6 | 10.0 | 8.4 | 9.0 | 9.0 | 8.6 | 10.5 |
| Oxygen Index | 19 | 19 | 19 | 19 | 19 | 19 | 19 |
| Initial K-Factor | 0.155 | 0.153 | 0.156 | 0.152 | 0.153 | 0.153 | 0.146 |
| K-Factor, Aged 1 Week at 158° F. @ 100% R.H. | 0.195 | 0.194 | 0.200 | 0.188 | 0.194 | 0.194 | 0.189 |

[6]Selectrofoam 6406 is a high functionality polyol derived from sucrose and amine; marketed by PPG.
[7]DC 193 is a silicone surfactant; marketed by Dow Corning.
[8]Freon 11B is chlorofluoromethane; marketed by DuPont.
[9]Hylene TIC is crude TDI; marketed by DuPont.
[10]Polycat 8 is the trademark of Abbott for dimethylcyclohexylamine.
[11]T-12 is the trademark of M & T for dibutyltin dilaurate.
[12]Mondur MR is the trademark of Mobay Chemical for polyisocyanate; functionality of 2.6, eq. wt. 131.

TABLE VII

| RIGID FOAM DATA | | | | | | | | |
|---|---|---|---|---|---|---|---|---|
| | 1 | 2 | 3 | 4 | 5 | 6 | 7 | 8 |
| Temp., °C. | 28 | 28 | 28 | 28 | 28 | 28 | 29 | 29 |
| 33-LV 0.75 .82 | .82 | — | — | — | — | — | — | — |
| T-1 0.07 | | | | | | | | |
| Polycat 8 1.5 } 1.57 T-1 0.07 | — | 1.57 | — | — | — | — | — | — |
| Rigid Foam Mix (g) | 157.5 | 157.5 | 157.5 | 157.5 | 157.5 | 157.5 | 157.5 | 157.5 |
| 50% (Ex 13) | — | — | .5 | — | — | — | — | — |
| 50% (Ex 12) | | | | | | .5 | .75 | — |
| 50% (Ex 10) | | | | | | | | .5 |
| 75% (Ex 7) | | | | | | | | |
| 50% T-1 | | | | .5 | — | — | — | — |
| 50% T-12 | | | | | .5 | — | — | — |
| [12]Mondur MR (g) | 100 | 100 | 100 | 100 | 100 | 100 | 100 | 100 |
| Initial | 42 | 41 | 32 | 30 | 39 | 47 | 40 | 45 |
| Strings | 85 | 70 | 60 | 55 | 70 | 80 | 65/70 | 75/80 |
| Tack Free | 105 | 85 | 85 | 70 | 105 | 100 | 80 | 105 |
| Rise | 115 | 105/110 | 105 | 90 | 115 | 110 | 105 | 130 |
| | 9 | 10 | 11 | 12 | 13 | 14 | 15 | 16 |
| Temp., °C. | 29 | 30 | 30 | 30 | 31 | 31 | 31 | 31 |
| Polycat 8 1.5 } 1.57 T-1 0.07 | — | — | — | — | — | — | — | 1.57 |
| Rigid Foam Mix (g) | 157.5 | 157.5 | 157.5 | 157.5 | 157.5 | 157.5 | 157.5 | 157.5 |
| 50% (Ex 13) | — | — | — | — | — | — | — | — |
| 50% (Ex 12) | — | — | — | — | — | — | — | — |
| 50% (Ex 10) | .75 | — | — | — | — | — | — | — |
| 75% (Ex 7) | | .5 | — | — | — | — | — | — |
| 50% (Ex 6) | | | .5 | .75 | 1.0 | 1.0* | .75* | — |
| [12]Mondur MR (g) | 100 | 100 | 100 | 100 | 100 | 100 | 100 | 100 |
| Initial | 38 | 37 | 48 | 45 | 37 | 37 | 45 | 37 |

TABLE VII-continued

RIGID FOAM DATA

| Strings | 70 | 68 | 85 | 75 | 65 | 60/65 | 75 | 65 |
|---|---|---|---|---|---|---|---|---|
| Tack Free | 85/90 | 75/80 | 110 | 95 | 80 | 75/78 | 95 | 75/80 |
| Rise | 105 | 100 | 135 | 125 | 105 | 95/100 | 120 | 105 |

*50% dioctyl phthalate

TABLE VIII

Physical Properties on Hand Mixed Rigid Foams Made with Amino and Amidotin Carboxylates

| Formulation 3 | pbw |
|---|---|
| Voranol 370 | 111 |
| Fluorocarbon 11SBA | 46 |
| DC-193 | 1.5 |
| Catalyst | As Shown |
| Mondur MR | 100 |

| Catalyst | Concentration, pbw | | | | | | |
|---|---|---|---|---|---|---|---|
| DABCO 33-LV | 0.75 | | | | | | |
| T-1 | 0.07 | | | | | | |
| Polycat 8 | | 1.5 | | | | | |
| T-1 | | 0.07 | | | | | |
| 50% T-12 in DOP | | | 0.5 | | | | |
| 50% Example 12 | | | | 0.75 | | | |
| 50% Example 10 | | | | | 0.75 | | |
| 50% Example 7 | | | | | | 0.75 | |
| 50% Example 6 | | | | | | | 1.0 |
| Density, lbs/cu. ft. | 1.92 | 1.96 | 1.94 | 1.90 | 1.96 | 1.90 | 1.94 |
| Oxygen Index | 20 | 20 | 20 | 20 | 20 | 20 | 20 |
| Dimensional Stability at 158° F. @ 100% R.H. | | | | | | | |
| 1 Day, % Vol. Change | 5.5 | 6.6 | 6.0 | 7.0 | 7.07 | 6.94 | 6.44 |
| 7 Days, % Vol. Change | 9.9 | 10.72 | 10.10 | 10.6 | 11.5 | 9.98 | 9.86 |
| Initial K-Factor | 0.155 | 0.158 | 0.166 | 0.153 | 0.160 | 0.155 | 0.174 |
| Aged K-Factor, 1 Week | 0.189 | 0.188 | 0.207 | 0.194 | 0.204 | 0.198 | 0.200 |

Voranol 370 is polyol; Hyd. No. 355–385; marketed by Dow.
Fluorocarbon 11SBA is stabilized fluorochloromethane; marketed by Allied.

EXAMPLE 17

A reaction injection molding formulation for the production of automotive bumper fascia was chosen for comparing the behavior of the compounds of this invention to the commercial catalyst dibutyltin dilaurate. The composition of the formulation used was as follows:

| Formulation 5 | |
|---|---|
| Component | pbw |
| (13)Pluracol 380 | 100.0 |
| 1,4-butanediol | 23.0 |
| Catalyst | 0.025 |
| (14)Mondur CD | 79.5 |

(13)Pluracol 380 - high mol. wt. triol; marketed by BASF Wyandotte
(14)Mondur CD - carbodiimide containing isocyanate; marketed by Mobay Plots of gel time and tack free time versus temperature in the range 70° to 100° F. clearly show that the catalyst of the invention activated by heat more than standard catalyst T-12, a feature that is very desirable in that it allows time to fill the mold with rapid cure and thus a shorter cycle.

EXAMPLE 18

The desirable delayed action behavior of the compounds of the present invention was demonstrated in yet another formulation. This formulation is typical of those used in making urethane shoe soles. Its composition is as follows:

| Component | pbw |
|---|---|
| (15)Voranol 4701 | 100.0 |
| 1,4-butanediol | 10.0 |
| (16)Freon R-11B DuPont | 7.0 |
| (17)L-5303 | 1.0 |
| Catalyst | as shown in table |
| (18)Isonate 181 | 51.0 |

(15)Voranol 4701 is Dow polyol; Hyd. No. 31.7–36.3 triol.
(16)Freon R11-B is DuPont's chlorofluoromethane.
(17)L-5303 is silicone surfactant; marketed by Union Carbide.
(18)Isonate 181 is aromatic isocyanate; marketed by Upjohn. % NCO content by wt. = 22.8; eq. wt. 184.

The premix including the catalyst was mixed with the isocyanate for 10 seconds, then poured into a preheated aluminum maze mold of 12"×12"×¼". The temperature of the mold surface at the time the reaction mixture was poured was 150° F. The flow of material inside the mold was followed by recording the time when it oozes out of the four vent holes at each corner of the mold. Demold time was varied and Shore A hardness was recorded immediately after demolding. Table IX summarizes data obtained.

TABLE IX

Evaluation of Experimental Amino Tin Catalysts
vs. UL-1 (dibutyltin dilaurate)
Temperature of Resin 86–87° F.

| Catalyst | Concent. php polyol | Time Material Extrudes from Vent Holes, secs | | | | Demold Time, mins | Shore A |
|---|---|---|---|---|---|---|---|
| | | 1st VH | 2nd VH | 3rd VH | 4th VH | | |
| Dibutyltin dilaurate | 0.03 | 43 | 44 | 48 | | 3* | 35 |
| | 0.03 | 43 | 45 | 47 | | 5* | 39 |
| Catalyst of Example 6 | 0.03 | 29 | 31 | 33 | 36 | 5 | 38 |
| Catalyst of Example 12 | 0.03 | 28 | 30 | 33 | 35 | 7 | 45 |
| Catalyst of Example 7 | 0.03 | 31 | 32 | 35 | 37 | 3 | 34 |

*Mold was never completely filled and thus material did not flow far enough to reach the 4th venting hole.

It is clear from the above table that compounds of the present invention provide for better flow (shorter time to fill mold) than commercial catalyst dibutyltin dilaurate.

EXAMPLE 19

The versatility of the catalysts of the present invention was ascertained by evaluating them in a variety of flexible foams. The formulations chosen were those of water-Freon and water-methylene chloride blown systems. The composition of these formulations and comparative reactivity data are shown in Tables X and XI.

It is clear from Tables X and XI that the compounds of the present invention are superior in activity to standard catalyst such as T-12. They also provide for longer cream time and/or shorter hard gel times than the combination of T-9-amine catalysts.

TABLE X

Freon-Water Blown Formulation

| Component | pbw |
|---|---|
| [19]Voranol 3010 | 100.0 |
| [20]Genetron 11SBA | 7.0 |
| Water | 3.6 |
| [21]L-6202 | 1.0 |
| Catalyst | As Shown |
| [22]Mondur T-80 | 47.0 |

TABLE X-continued

Freon-Water Blown Formulation

Premix Temp. 83° F.

| Catalyst | Concentration, pph Polyol | | | | | |
|---|---|---|---|---|---|---|
| T-9/DOP (½) | 1.0 | | | | 1.0 | |
| [23]DABCO TL | 0.2 | | | | 0.2 | |
| Example 10 | | 0.8 | | | | |
| Example 7 | | | 1.0 | 1.1 | | |
| Example 12 | | | | | | 0.4 |
| Reactivity | | | | | | |
| B.O.R., Secs. | 11 | 16 | 17 | 17 | 11 | 12 |
| Rise, Secs. | 110 | 100 | 100 | 100 | 105 | 100 |
| Hard Gel, Secs. | 115 | 92 | 110 | 100 | 105 | 95 |
| Rise Height, Inches | 8½ | | | 9¼ | | 9¼ |
| Foam Rating | Good Open Cells | Good Open Cells | Good Open Cells | Good Open Cells | Good Open Cells | Good Open Cells |

[19]Voranol 3010 is high molecular wt. triol; marketed by Dow Chemical Corporation.
[20]Genetron 11SBA is Allied Chemical chlorofluoromethane.
[21]L-6202 is Union Carbide Corporation silicone surfactant.
[22]Mondur T-80 is an aromatic isocyanate; marketed by Mobay Chemical.
[23]DABCO TL is a tertiary amine catalyst; marketed by Air Products and Chemicals, Inc.

TABLE XI

Methylene Chloride-Water Blown Formulation

| Component | pbw |
|---|---|
| Voranol 3010 | 100.0 |
| Methylene Chloride | 8.0 |
| Water | 3.6 |
| Silicone L-6202 | 1.5 |
| Catalyst | As Shown |
| Mondur T-80 | 41.6 |
| Premix Temp. | 72° F., 80° F. |

| Catalyst | Concentration, pph Polyol | | | | | | |
|---|---|---|---|---|---|---|---|
| 50% T-9 in DOP | 0.8 | * | | | | | |
| DABCO TL | 0.4 | 0.1 | 0.1 | 0.2 | 0.2 | 0.1 | 0.1 |
| T-12 | | 0.3 | | | | | |
| 50% (Example 10) | | | 1.6 | 0.8 | | | |
| 50% (Example 7) | | | | | 0.6 | | 0.6 |
| Reactivity | | | | | | | |
| B.O.R., Secs. | 13 | 22 | 17 | 17 | 19 | 22 | 19 |
| Rise, Secs. | 95 | 120 | 110 | 95 | 95 | 110 | 90 |
| Hard Gel, Secs. | 105 | 145 | 100 | 100 | 100 | 120 | 105 |
| Rise Height, Inches | 8½ | 8¾ | 9½ | 8½ | 8½ | 8¾ | 8¾ |
| Foam Rating | Good | Good | Good Open Cells | Good Open Cells | Good Open Cells | Good Open Cells | Good Open Cells |

* Premix temp. = 78° F.

What is claimed is:

1. The method of catalyzing the reaction between an organic isocyanate and an organic compound having at least one active hydrogen containing group, which comprises effecting said reaction in the presence of a catalytic amount of an organotin compound corresponding to either of the formulae set out below:

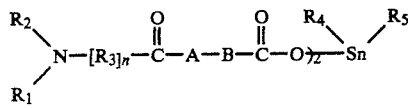

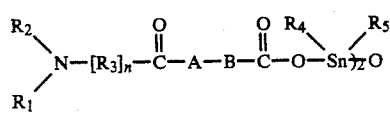

wherein $R_1$ and $R_2$ are independently H, alkyl of 1 to 20 carbon atoms; hydroxyalkyl of 2 to 20 carbon atoms; or $R_1$ and $R_2$ together with N form a nitrogen-containing heterocyclic ring of 5 or 6 atoms:

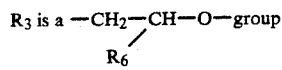

in which n equals zero or one and $R_6$ is hydrogen or an alkyl or an alkyl hydrocarbyl group of up to 20 carbon atoms;

A and B are carbon atoms linked by a single or double bond or together comprise part of a six membered ring from the group consisting of cyclohexane, cyclohexene and benzene;

$R_4$ and $R_5$ are independently alkyl groups of 1 to 20 carbon atoms, phenyl or cycloalkyl groups of 6 to 20 carbon atoms.

2. The method as defined in claim 1 wherein said organotin compound corresponds to the formula below:

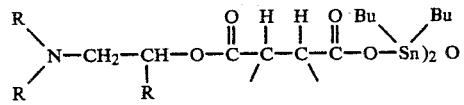

in which each R is a substituent from the group consisting of methyl and ethyl.

3. The method as defined in claim 1 wherein said organotin compound corresponds to the formula below:

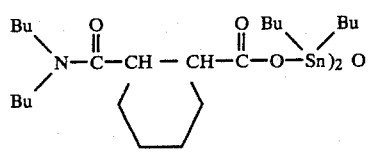

4. The method as defined in claim 1 wherein said organotin compound corresponds to the formula below:

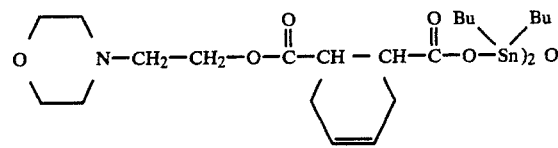

5. The method as defined in claim 1 wherein said organotin compound corresponds to the formula below:

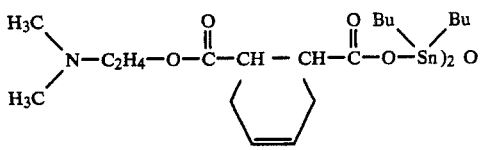

6. The method as defined in claim 1 wherein said organotin compound corresponds to the formula below:

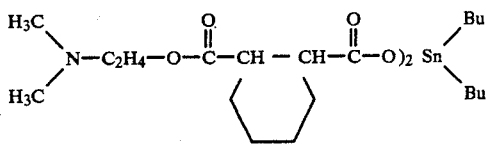

7. In a one shot composition for the preparation of flexible polyurethane foam comprising:
polyol
diisocyanate
silicone cell stabilizer
water and/or fluorocarbon blowing agent
the improvement comprising an organotin catalyst corresponding to either of the formulae below:

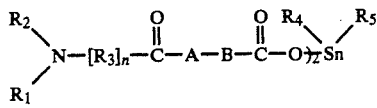

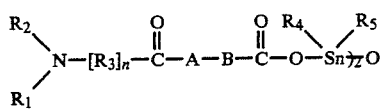

wherein $R_1$ and $R_2$ are independently H, alkyl of 1 to 20 carbon atoms; hydroxyalkyl of 2 to 20 carbon atoms; or $R_1$ and $R_2$ together with N form a nitrogen-containing heterocyclic ring of 5 or 6 atoms;

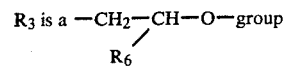

in which n equals zero or one and $R_6$ is hydrogen or an alkyl or an alkyl hydrocarbyl group of up to 20 carbon atoms;

A and B are carbon atoms linked by a single or double bond or together comprise part of a six membered ring from the group consisting of cyclohexane, cyclohexene and benzene;

R4 and R5 are independently alkyl groups of 1 to 20 carbon atoms, phenyl or cycloalkyl groups of 6 to 20 carbon atoms.

8. In a composition for the preparation of rigid polyurethane foam comprising:
high functionality polyol
silicone cell stabilizer
fluorocarbon blowing agent
isocyanate the improvement comprising an organotin catalyst corresponding to either of the formulae below:

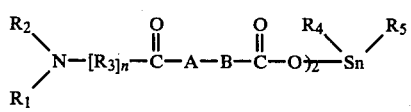

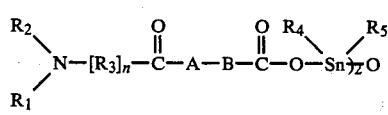

wherein $R_1$ and $R_2$ are independently H, alkyl of 1 to 20 carbon atoms; hydroxyalkyl of 2 to 20 carbon atoms; or $R_1$ and $R_2$ together with N form a nitrogen-containing heterocyclic ring of 5 or 6 atoms;

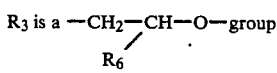

in which n equals zero or one and $R_6$ is hydrogen or an alkyl or an alkyl hydrocarbyl group of up to 20 carbon atoms;

A and B are carbon atoms linked by a single or double bond or together comprise part of a six membered ring from the group consisting of cyclohexane, cyclohexene and benzene;

R4 and R5 are independently alkyl groups of 1 to 20 carbon atoms, phenyl or cycloalkyl groups of 6 to 20 carbon atoms.

9. In a premix composition for the preparation of flexible foam comprising:
polyol
methylene chloride
silicone surfactant
water the improvement comprising a catalytic amount of an organotin catalyst corresponding to either of the formulae below:

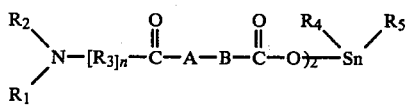

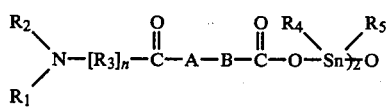

wherein $R_1$ and $R_2$ are independently H, alkyl of 1 to 20 carbon atoms; hydroxyalkyl of 2 to 20 carbon atoms; or $R_1$ and $R_2$ together with N form a nitrogen-containing heterocyclic ring of 5 or 6 atoms;

$R_3$ is a $-CH_2-CH-O-$ group
               |
               $R_6$ in which n equals zero or one and $R_6$ is hydrogen or an alkyl or an alkyl hydrocarbyl group of up to 20 carbon atoms;

A and B are carbon atoms linked by a single or double bond or together comprise part of a six membered ring from the group consisting of cyclohexane, cyclohexene and benzene;

R4 and R5 are independently alkyl groups of 1 to 20 carbon atoms, phenyl or cycloalkyl groups of 6 to 20 carbon atoms, said premix being reactable with organic polyisocyanate to form polyurethane.

10. In a reaction injection molding formulation comprising:
high molecular weight polyol
diol or diamine chain extending agent
fluorocarbon
diisocyanate the improvement comprising a catalytic amount of an organotin catalyst corresponding to either of the formulae below:

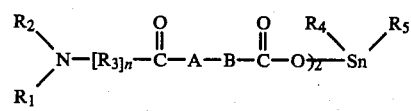

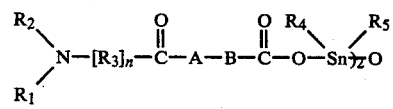

wherein $R_1$ and $R_2$ are independently H, alkyl of 1 to 20 carbon atoms; hydroxyalkyl of 2 to 20 carbon atoms; or $R_1$ and $R_2$ together with N form a nitrogen-containing heterocyclic ring of 5 or 6 atoms;

$R_3$ is a $-CH_2-CH-O-$ group
               |
               $R_6$ in which n equals zero or one and $R_6$ is hydrogen or an alkyl of an alkyl hydrocarbyl group of up to 20 carbon atoms;

A and B are carbon atoms linked by a single or double bond or together comprise part of a six membered ring from the group consisting of cyclohexane, cyclohexene and benzene;

R4 and R5 are independently alkyl groups of 1 to 20 carbon atoms, phenyl or cycloalkyl groups of 6 to 20 carbon atoms.

11. In the catalyzed reaction between an organic polyol and an organic polyisocyanate for the formation of polyurethane foam, the improvement which comprises employing in said reaction a catalytic amount of a catalyst composition comprising a tertiary amine and an organotin compound corresponding to either of the formulae set out below:

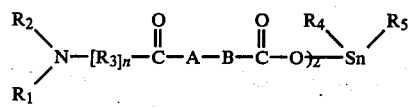

-continued

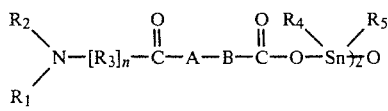

wherein $R_1$ and $R_2$ are independently H, alkyl of 1 to 20 carbon atoms; hydroxyalkyl of 2 to 20 carbon atoms; or $R_1$ and $R_2$ together with N form a nitrogen-containing heterocyclic ring of 5 or 6 atoms;

$R_3$ is a $-CH_2-\underset{\underset{R_6}{|}}{CH}-O-$ group in which n equals zero or one and $R_6$ is hydrogen or an alkyl or an alkyl hydrocarbyl group of up to 20 carbon atoms;

A and B are carbon atoms linked by a single or double bond or together comprise part of a six membered ring from the group consisting of cyclohexane, cyclohexene and benzene;

$R_4$ and $R_5$ are independently alkyl groups of 1 to 20 carbon atoms, phenyl or cycloalkyl groups of 6 to 20 carbon atoms.

12. The method as defined in claim 11 wherein said tertiary amine comprises triethylenediamine.

* * * * *

UNITED STATES PATENT AND TRADEMARK OFFICE
CERTIFICATE OF CORRECTION

PATENT NO. : 4,430,456

DATED : February 7, 1984

INVENTOR(S) : Ibrahim S. Bechara and Rocco L. Mascioli

It is certified that error appears in the above-identified patent and that said Letters Patent is hereby corrected as shown below:

In Claims 2, 3, 4, 5 and 6

The formula is missing the horizontal line which indicates the bond between the tin atom (Sn) and the oxygen atom (O)

Column 20, Line 47

After "alkyl" delete "of" and substitute therefor -- or --

Signed and Sealed this

Eighteenth Day of September 1984

[SEAL]

Attest:

GERALD J. MOSSINGHOFF

Attesting Officer

Commissioner of Patents and Trademarks